US00PP13905P29

(12) United States Plant Patent
Turner

(10) Patent No.: US PP13,905 P2
(45) Date of Patent: Jun. 24, 2003

(54) BRACTEANTHA PLANT NAMED 'COPPER'

(75) Inventor: Matthew Turner, Penrith South (AU)

(73) Assignee: Oasis Horticulture Pty. Ltd. (AU)

( * ) Notice: Subject to any disclaimer, the term of this patent is extended or adjusted under 35 U.S.C. 154(b) by 0 days.

(21) Appl. No.: 10/109,495

(22) Filed: Mar. 27, 2002

(51) Int. Cl.[7] ..... A01H 5/00
(52) U.S. Cl. ..... Plt./359

(58) Field of Search ..... Plt./359

*Primary Examiner*—Bruce R. Campell
*Assistant Examiner*—Susan B. McCormick
(74) *Attorney, Agent, or Firm*—Wood, Phillips, Katz, Clark & Mortimer

(57) ABSTRACT

A new and distinct Bracteantha plant named 'Copper', characterized by its yellow-orange colored involucral bracts, yellow disc florets, upright mounded growth habit, and dark green leaves.

1 Drawing Sheet

LATIN NAME OF THE GENUS AND SPECIES OF PLANT CLAIMED

*Bracteantha bracteata.*

VARIETY DEMONINATIION

'Copper'.

BACKGROUND OF THE INVENTION

The present invention comprises a new and distinct Bracteantha plant, botanically known as *Bracteantha bracteata* and hereinafter referred to by the cultivar name 'Copper'.

The new cultivar was developed by the inventor in a controlled breeding program at New South Wales, Australia in March, 1998.

The female (seed) parent of 'Copper' was the cultivar 'Nullabor Flame' (not patented in the United States), characterized by its tall growth habit and numerous red bracts. The male (pollen) parent of 'Copper' was the cultivar 'Diamond Head' (not patented in the United States), characterized by its semi-prostrate habit and low number of yellow bracts. 'Copper' was selected as one of the flowering progeny of the above cross on Aug. 1, 1998.

Asexual reproduction of the new cultivar by terminal cuttings, at West Chicago, Ill., has demonstrated that the characteristics of the new cultivar as herein described are firmly fixed and retained through successive generations of such asexual propagation.

SUMMARY OF THE INVENTION

It was found that the cultivar of the present invention:

(a) exhibits yellow-orange involucral bracts and yellow disc florets;

(b) forms dark green foliage;

(c) exhibits a good basal branching character; and (d) exhibits an upright mounded growth habit.

When the new cultivar of the present invention is compared to 'Cream' (disclosed in U.S. Plant patent application Ser. No. 09/819,340) it is found that the new cultivar has smaller leaves and smaller flowers of a darker orange color. The new cultivar can also be compared to its sibling, 'Yellow' (disclosed in a concurrent patent application). In side-by-side comparisons, the involucral bracts of the new cultivar are more orange than the bracts of 'Yellow'.

BRIEF DESCRIPTION OF PHOTOGRAPH

The accompanying photograph show as nearly true as it is reasonably possible to make the same in color illustrations of this type, typical flower and foliage characteristics of the new cultivar. The photograph illustrates two plants in one pot, grown for 10 weeks in a greenhouse at West Chicago, Ill.

DETAILED BOTANICAL DESCRIPTION

The new cultivar has not been observed under all possible environmental conditions to date. Accordingly, it is possible that the phenotype may vary somewhat with variations in the environment, such as temperature, light intensity, and day length.

The chart used in the identification of colors described herein is The R.H.S. Colour Chart of The Royal Horticultural Society, London, England. The color values were determined on Feb. 6, 2002. The readings were taken between 10:00 and 11:00 a.m. under natural daylight conditions. The plants were produced from cuttings taken from stock plants and grown for 12 weeks in a double polycarbonate covered greenhouse under conditions comparable to those used in commercial practice while utilizing a soilless growth medium. Temperatures of approximately 65° to 75° (18° to 24° C.) during the day and approximately 55° to 60° F. (13° to 16° C.) during the night and light levels of between 5,000 and 8,000 footcandles were maintained.

Classification:
*Botanical.*—*Bracteantha bracteata* cultivar 'Copper'.
*Commercial.*—Helichrysum.

Parentage:
*Female parent.*—'Nullabor Flame'.
*Male parent.*—'Diamond Head'.

Propagation:
*Type cutting.*—Terminal tip.
*Time to initiate roots.*—Approximately 21 to 30 days with the shorter times generally being experienced in the summer and the longer times in the winter.

Plant description:

*Form.*—Upright, mounded.

*Habit of growth.*—Moderate. A mature plant, 12 weeks after the planting of a rooted cutting, commonly measures approximately 20.8 cm in height and approximately 37.4 cm in diameter.

*Branching habit.*—Freely basal branching although pinching improves basal branching. Commonly develops approximately 4 lateral branches.

*Lateral branch.*—Length: Approximately 18.8 cm. Diameter: Approximately 5 mm with hirsute pubescence. Color: 145B. Internode length: Approximately 6 mm.

*Foliage.*—Arrangement: Alternate. Shape: Linear with entire margin, acute apex and clasping base. Size: Approximately 4.8 cm in length and approximately 7 mm at widest point. Texture: Upper surface is rough and lower surface is smooth. Color: Upper surface is darker than 147A and lower surface is147B. Midvein on lower surface is moderately pubescent. Venation of both surfaces: Closest to 145B.

Flowering description:

*Flowering habit.*—Freely flowering.

*Natural flowering season.*—Spring through fall.

Flower description:

*Inflorescence type.*—Single, composite.

*Flowers arrangement.*—Acropetally on a capitulum.

*Bud.*—Size: 1.6 cm in length, 1.5 cm in diameter. Color: 163D at base, 183B at tip.

*Inflorescence diameter.*—Approximately 2.9 cm.

*Inflorescence depth.*—Approximately 1.8 cm.

*Involucral bracts.*—Quantity: Approximately 115 arranged in 10 whorls. Aspect: Appear flat at maturity then become downwardly pointing with age. Texture: Smooth, papery. Shape: Linear. Size: Length — 1.2 cm, width varies from 1 mm (inner whorl) to 4 mm (outer whorl). Color — Upper surface, fully opened involucral bract: 15B at base, 168B in center and 169A at tip. Lower surface: 163B at base, 163A in center and 166A at tip.

*Disc diameter.*—1.5 cm.

*Disc florets.*—Shape: Tubular. Length: Approximately 7 mm. Color: 23A.

*Peduncle.*—Length: Approximately 6.2 cm. Diameter: Approximately 2 mm. Strength: Good. Aspect: Erect. Color: 144B. Texture: Densely pubescent.

*Fragrance.*—None.

*Reproductive organs.*—Androecium: One stamen per disc floret. Anther color: 25A. Pollen color: 12A. Gynoecium: One pistil per disc floret. Stigma shape: Bilobate. Stigma color: 21B. Style length: Approximately 5 mm. Style color: 1B.

Disease resistance: Resistance to diseases common to Helichrysum has not been observed.

Seed production: Seed production has not been observed.

I claim:

1. A new and distinct Bractheantha plant named 'Copper' substantially as herein shown and described, which:

(a) Exhibits yellow-orange involucral bracts and yellow disc florets;

(b) Forms dark green foliage;

(c) Exhibits a good basal branching character; and (d) Exhibits an upright mounded growth habit.

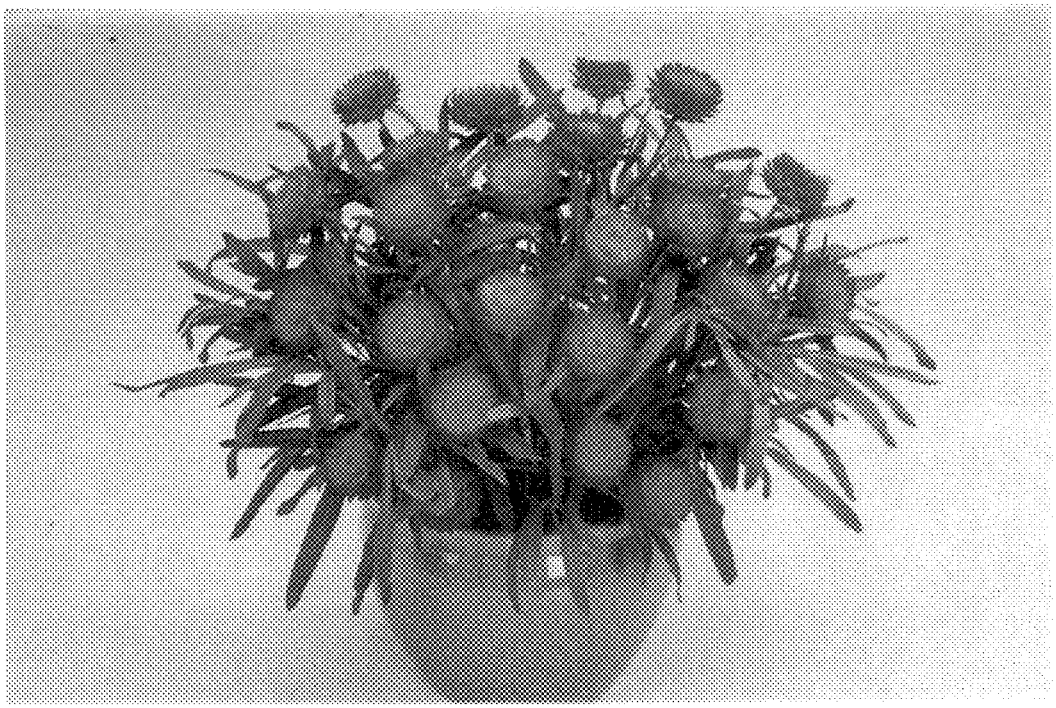

* * * * *